United States Patent
Cheng et al.

(10) Patent No.: US 9,226,935 B2
(45) Date of Patent: Jan. 5, 2016

(54) METHODS FOR MODULATING THE EXPRESSION AND AGGREGATION OF A CAG-EXPANDED GENE PRODUCT IN CELLS AND METHODS FOR IDENTIFYING AGENTS USEFUL FOR DOING THE SAME

(71) Applicants: Tzu-Hao Cheng, Taipei (TW); Chia-Rung Lu, Taipei (TW); Tzu-Han Wang, Taipei (TW); Stanley N. Cohen, Stanford, CA (US)

(72) Inventors: Tzu-Hao Cheng, Taipei (TW); Chia-Rung Lu, Taipei (TW); Tzu-Han Wang, Taipei (TW); Stanley N. Cohen, Stanford, CA (US)

(73) Assignees: NATIONAL YANG MING UNIVERSITY, Taipei (TW); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 13/936,696

(22) Filed: Jul. 8, 2013

(65) Prior Publication Data

US 2013/0331437 A1  Dec. 12, 2013

Related U.S. Application Data

(62) Division of application No. 13/110,494, filed on May 18, 2011, now Pat. No. 8,569,254.

(30) Foreign Application Priority Data

Dec. 10, 2010  (TW) .............................. 099143336 A

(51) Int. Cl.
- *A61P 25/00* (2006.01)
- *A61K 31/713* (2006.01)
- *C12N 15/113* (2010.01)
- *C12Q 1/68* (2006.01)
- *A61K 51/10* (2006.01)

(52) U.S. Cl.
CPC ............ *A61K 31/713* (2013.01); *C12N 15/113* (2013.01); *A61K 51/10* (2013.01); *A61K 51/1075* (2013.01); *C12N 2310/14* (2013.01)

(58) Field of Classification Search
None
See application file for complete search history.

*Primary Examiner* — Sean McGarry
(74) *Attorney, Agent, or Firm* — Muncy, Geissler, Olds & Lowe, P.C.

(57) ABSTRACT

This invention provides a method for modulating the expression of a first gene in a cell wherein the first gene is one containing more than 36 CAG trinucleotide repeats and encoding a protein that form polyglutamine-mediated protein aggregation. Suppression of the first gene is achieved by reducing the expression of SPT4 gene or SUPT4H gene. It can also be achieved by inhibiting the formation of a Spt4/Spt5 complex or a Supt4h/Supt5h complex. Also provided is a method for identifying an agent useful for modulating the expression and aggregation of CAG-expanded gene product, or treating a polyglutamine disease such as Huntington's disease.

7 Claims, 9 Drawing Sheets

SEQUENCE LISTING

```
<160> NUMBER OF SEQ ID NOS: 7

<210> SEQ ID NO 1
<211> LENGTH: 19
<212> TYPE: RNA
<213> ORGANISM: Artificial Sequence
<220> FEATURE:
<223> OTHER INFORMATION: Supt4h siRNA

<400> SEQUENCE: 1
cuauagacca guucgaaua                                              19

<210> SEQ ID NO 2
<211> LENGTH: 19
<212> TYPE: RNA
<213> ORGANISM: Artificial Sequence
<220> FEATURE:
<223> OTHER INFORMATION: Supt4h siRNA

<400> SEQUENCE: 2
ucaaauacca auaaagcga                                              19
```

```
<210> SEQ ID NO 3
<211> LENGTH: 19
<212> TYPE: RNA
<213> ORGANISM: Artificial Sequence
<220> FEATURE:
<223> OTHER INFORMATION: Supt4h siRNA

<400> SEQUENCE: 3
gggagugucu gggcggauu                                                    19

<210> SEQ ID NO 4
<211> LENGTH: 19
<212> TYPE: RNA
<213> ORGANISM: Artificial Sequence
<220> FEATURE:
<223> OTHER INFORMATION: Supt4h siRNA

<400> SEQUENCE: 4
cccaaggaau cgugcggga                                                    19

<210> SEQ ID NO 5
<211> LENGTH: 21
<212> TYPE: RNA
<213> ORGANISM: Artificial Sequence
<220> FEATURE:
<223> OTHER INFORMATION: Supt4h siRNA

<400> SEQUENCE: 5
uggccuacaa aucgagagau u                                                 21

<210> SEQ ID NO 6
<211> LENGTH: 21
<212> TYPE: DNA
<213> ORGANISM: Artificial Sequence
<220> FEATURE:
<223> OTHER INFORMATION: control sequence that does not target any gene

<400> SEQUENCE: 6
uucuccgaac gugucacgut t                                                 21

<210> SEQ ID NO 7
<211> LENGTH: 21
<212> TYPE: DNA
<213> ORGANISM: Artificial Sequence
<220> FEATURE:
<223> OTHER INFORMATION: control sequence that does not target any gene

<400> SEQUENCE: 7
acgugacacg uucggagaat t                                                 21
```

METHODS FOR MODULATING THE EXPRESSION AND AGGREGATION OF A CAG-EXPANDED GENE PRODUCT IN CELLS AND METHODS FOR IDENTIFYING AGENTS USEFUL FOR DOING THE SAME

CROSS-REFERENCE TO RELATED APPLICATIONS

This application is a divisional of U.S. patent application Ser. No. 13/110,494, filed May 18, 2011, which claims priority under 35 U.S.C. §119(a) on Patent Application No(s). 099143336 filed in Taiwan, Republic of China, on Dec. 10, 2010, the entire contents of which are hereby incorporated by reference.

SEQUENCE LISTING

This invention contains sequence listing.

FIELD OF THE INVENTION

This invention relates to methods for modulating the expression of genes containing expanded CAG repeats in cells. This invention also provides methods for modulating or preventing polyglutamine-mediated protein aggregation, as well as methods for identifying agents useful in practicing said modulating methods.

BACKGROUND OF THE INVENTION

Polyglutamine (PolyQ) diseases are a class of diseases consisting of nine genetically distinct disorders. They include Huntington's disease (HD), dentatorubral-pallidoluysian astrophy (DRPLA), SBMA and spino-cerebellar ataxia 1, 2, 3, 6, 7 and 17 (SCA1/2/3/6/7/17). Because these diseases are caused by the expansion of a translated CAG repeats that codes for the glutamines, they are also known as CAG repeat diseases.

One common physiological characteristic shared among these genetically distinct diseases is that patients who suffer from the diseases are all found to have proteinaceous deposits in their brains. Although in each of these diseases, the proteinaceous deposit is associated with a different protein, the proteins all contain an expanded stretch of glutamines. To date, this expanded stretch of polyQ sequence in the disease-related proteins is the only known genetic mutation implicated in all the polyQ diseases.

In general, the number of CAG repeats in genes can range from a benign number of less than 36 to a pathological number of 37 or more. The larger number of CAG repeats are thought to correlate to pathological phenotypes because proteins and polypeptides that contain a long stretch of glutamines have an inherit propensity to form amyloid-like fibrils (polymerization of protein aggregates with β-sheet structure) in vitro (Scherzinger et al., 1997), and mutant proteins with an expanded polyQ tract are thought to result in a distinct protein conformation that leads to aggregation and eventual neuronal cell death (Zoghbi and Orr, 2000).

In human, expanded polyQ mutant proteins are expressed widely in cells of the central nervous system (CNS), however, in each different disease, a specific population of neurons is more vulnerable than others. Consequently, the difference in vulnerability results in characteristic patterns of neurodegeneration and clinical features for each of the nine different diseases. The severity of the disease may correlate to the number of CAG repeats. For example, in HD, CAG repeat numbers between 28-35 are considered to be intermediate, 35-40 are considered reduced penetrance, and repeat numbers greater than 40 are considered to be full penetrance.

Table 1 lists eight diseases caused by the expanded CAG repeats, the affected genes, and their defining pathogenic repeat length. SCA6 is not included in this list because unlike other polyQ diseases, the length of CAG repeat in SCA6 is not a determining factor for the age that symptoms begin to present. Pathological repeat length in SCA6 is also much shorter than the other polyQ diseases, where a number between 21-30 is sufficient to cause pathological phenotype.

TABLE 1

| Disease | | Gene name/ protein product | Pathogenic repeat length |
|---|---|---|---|
| Spinocerebellar ataxia type 1 | SCA1 | SCA1/ataxin 1 | 40~82 |
| Spinocerebellar ataxia type 2 | SCA2 | SCA2/ataxin 2 | 32~200 |
| Spinocerebellar ataxia type 3 | SCA3(MJD) | SCA3/ataxin 3 | 61~84 |
| Spinocerebellar ataxia type 7 | SCA7 | SCA7/ataxin 7 | 37~306 |
| Spinocerebellar ataxia type 17 | SCA17 | SCA17/TBP | 47~63 |
| Dentatorubral pallidoluysian atrophy | DRPLA | DRPLA/ atrophin 1 | 49~88 |
| Spinal and bular muscular atrophy | SBMA | AR/androgen receptor | 38~62 |
| Huntington's disease | HD | Htt/huntingtin | 40~121 |

Of the above eight diseases, HD is perhaps the most well-known among the general public because of its devastating effects on the patients. The disease is associated with selective neuronal cell death occurring primarily in the cortex and striatum. It is a fatal and cruel disease that progressively deprives the patient of his movement, cognition, and personality, exacting significant economic and emotion tolls on the patient and his family. The frequency of HD is particularly prevalent among people of Western European descent (about 1 in 20,000). Unfortunately, there is presently no cure for this terrible disease.

Currently, available treatments for HD are mainly limited to managing the macroscopic symptoms. For example, one of the newest compound approved by the FDA, tetrabenazine, is a drug for reducing hyperkinetic movements in HD patients. Tetrabenazine is a vesicular monoamine transporter (VMAT) inhibitor which promotes early degradation of neurotransmitters. Thus, the drug merely treats the symptom, not the root of the disease. Other drugs currently used for treating HD include neuroleptics and benzodiazepines. As the disease progresses, an ever wider range of pharmacopeia is needed to address different symptoms, including antipsychotics, and drugs for hypokinesia. No presently known treatment is attempting to address the root cause of HD.

As mentioned above, the root cause of HD is an abnormal expansion of CAG repeats in a gene within the CNS cells, specifically the gene Htt which encodes the protein huntingtin (Htt). In a normal person, there are about 8-25 constitutive repeats of CAG nucleotide sequence in the Htt gene. In a HD patient, the number of CAG repeats are expanded to 36 or more. Because this type of mutation is dominant, a person only needs to inherit one copy of the mutated huntingtin gene to develop HD.

Recent cell and animal model studies have shown that aggregates formed by mutant Htt play a critical role in the progression of HD. It has been observed that the mutant Htt proteins can leave behind shorter fragments from parts of the polyQ expansion when subjected to proteolytic cleavages. If too many copies of glutamine exist in the mutant Htt, the polar nature of glutamine will lead to undesirable interactions with other proteins. In particular, mutant Htt with too many copies of glutamines will form hydrogen bonds with one another and aggregate rather than fold into functional proteins. Over time, the accumulated protein aggregates will damage the neuronal cells, leading to cell death and neurological deficit in the patient. The damaging effects of the protein aggregates have been corroborated by experiments showing that chemical reagents capable of inhibiting the formation of protein aggregates can enhance survival of cells and ameliorate pathology of HD in a mouse model (Sanchez et al., 2003; Tanaka et al., 2004).

Besides using inhibitory molecules to prevent protein aggregation, reducing the expression of mutant huntingtin gene is in principle an alternative way to inhibit the genesis of insoluble protein aggregates. In vitro studies have shown that the extent of polyQ protein aggregation is related to protein concentration (Scherzinger et al., 1999). Therefore, by lowering the level of mutant huntingtin gene expression, a lower level of expanded PolyQ protein will be expressed, which in turn is likely to reduce protein aggregate formation and delay the onset of HD.

These findings point to a potentially simple and powerful strategy of combating HD pathogenesis by modulating the formation of insoluble protein aggregates resulting from CAG repeat mutation in Htt. For example, a therapeutic agent that can modulate the expression of the polyQ mutant genes or formation of the polyQ aggregates can potentially address the root cause of the polyQ diseases, not just their physiological symptoms. Unfortunately, the lack of knowledge about cellular factors and agents that can modulate the expression of the mutant polyQ genes has prevented practical development of this therapeutic strategy.

Therefore, there still exists urgent needs for methods and tools that can modulate or reduce the expression of genes suffering from expanded CAG repeat mutations as well as methods and tools for identifying and developing agents that are effective at modulating or reducing the expression of the mutant genes.

SUMMARY OF THE INVENTION

In view of the above, it is an object of the present invention to provide methods and tools that can modulate or reduce the expression of genes containing expanded CAG repeats.

It is also an object of the present invention to provide treatment methods and therapeutic agents for treating polyQ diseases.

It is a further object of the present invention to provide methods and tools for screening and developing agents that are effective at modulating or reducing the expression of genes containing expanded CAG repeats.

The above objects of the present invention are satisfied by the unexpected discovery that the microbial transcription elongation factor Spt4 and its mammalian ortholog, Supt4h, play a modulating role in the expression of genes containing expanded CAG repeats.

Specifically, the inventors have found that the expression of genes containing expanded CAG repeats and the aggregation of proteins with an expanding stretch of polyQ sequence are both attenuated in Spt4-/Supt4h-deficient cells. The inventors further discovered that Spt4/Supt4h have negligible effect on genes containing short or no CAG repeats. These unexpected discoveries establish Spt4/Supt4h as useful targets for polyQ disease intervention.

In another discovery of the invention, the inventors have also found that the attenuation effects of Spt4-/Supt4h-deficiency can be attributed to impaired transcription elongation in the CAG expanded gene, leading to decreased corresponding mRNA and protein production. This discovery enables a coherent view of several known properties of Spt4 and Supt4h which form the basis of a mechanistic model that guides the design of therapeutic approaches of the present invention.

For example, several recent studies have implicated Spt4 as playing a key role in the control mechanisms of transcription and heterochromatin formation in yeast cells (Crotti and Basrai, 2004; Rondon et al., 2003). Analysis of its effect on transcriptional control has shown that Spt4 is a positive regulator for the elongation process. Particularly, Spt4 promotes RNA polymerase II-mediated transcript synthesis from a DNA template that has a high percentage of GC content or is in a size of greater than 3 Kb in yeast cells (Rondon et al., 2003). Further recent evidences reveal that Spt4 affects RNA polymerase II processivity during transcription, which in turn identifies Spt4 as an important factor for the persistence of Pol II along chromatin templates (Mason and Struhl, 2005).

Without being bound to any particular theory, the inventors believe that the reason Spt4 is required for the expression of polyQ-containing proteins is due to its role in preventing premature dissociation of transcription machinery from those DNA templates that take a long time for Pol II to move through (e.g. templates containing a CAG-expanded region). This model explains the observation that Spt4-/Supt4h-deficient cells exhibit attenuated expressions of CAG-expanded genes. Accordingly, therapeutic methods can be advantageously devised by targeting Spt4 or Supt4h.

In yet another discovery of the present invention, the inventors have found that the attenuation effect of Spt4 deficiency can be recapitulated by a specific Spt5 mutant that has a defect to interact with Spt4. Because Spt4 usually form a complex with Spt5 in cells, this discovery further establishes that the Spt4/Spt5 complex is also a therapeutic target.

Based on the above various surprising discoveries of the present invention, the inventors have conceived and reduced to practice various tools and methods for modulating the expression of genes containing an expanded CAG repeat sequence.

Accordingly, in one aspect, the present invention provides a method for modulating the expression of a gene containing expanded CAG repeats with a repeat number greater than 36. Embodiments in accordance with this aspect of the invention generally seek to target a transcription elongation factor involved in the expression of genes containing expanded CAG repeats. Targeting of the transcription elongation factor can either be direct or indirect.

In some preferred embodiments, methods in accordance with this aspect of the invention generally include the step of suppressing the expression of a transcription elongation factor gene in a cell. The transcription elongation factor gene is preferably the SPT4 gene for an yeast cell or the SUPT4H gene for a mammalian cell. The expanded CAG gene is preferably one selected from the group consisting of SCA1, SCA2, SCA3, SCA7, SCA17, DRPLA, AR, and Htt gene, or a combination thereof.

In other preferred embodiments, methods in accordance with this aspect of the invention generally include the step of inhibiting the formation of an transcription elongation factor complex. The transcription elongation factor complex is preferably Spt4/Spt5 complex in a yeast cell or a Supt4h/Supt5h complex in a mammalian cell. The expanded gene is also preferably one selected from the group consisting of SCA1, SCA2, SCA3, SCA7, SCA17, DRPLA, AR, and Htt gene, or a combination thereof.

In still other preferred embodiments, methods in accordance with this aspect of the invention may include both steps of suppressing the transcription elongation factor and inhibiting the formation of the transcription factor complex related to expression of genes containing expanded CAG repeats. The transcription elongation factor gene is preferably SPT4 for a yeast cell or SUPT4H for a mammalian cell. The transcription factor complex is preferably Spt4/Spt5 in a yeast cell or Supt4h/Supt5h in a mammalian cell. The expanded gene is also preferably one selected from the group consisting of SCA1, SCA2, SCA3, SCA7, SCA17, DRPLA, AR, and Htt gene, or a combination thereof.

In another aspect, the present invention further provides a method for identifying a pharmaceutical agent useful for modulating the expression of genes containing expanded CAG repeats, or treating a polyglutamine disease. The expanded genes are preferably selected from the group consisting of SCA1, SCA2, SCA3, SCA7, SCA17, DRPLA, AR, and Htt gene. The number of CAG repeats is preferably greater than 36.

Methods in accordance with this aspect of the present invention generally include the step of testing a candidate compound to assess its effectiveness at disrupting formation of an Spt4/Spt5 complex or an Supt4h/Supt5h complex, and identifying said compound as a lead compound if it is effective at a predetermined level. Preferably, a protein-protein interaction assay is used for assessing the candidate compound's effectiveness.

Other aspects and advantages of the invention will be apparent from the following description and the appended claims.

DETAILED DESCRIPTION

Figure 1:
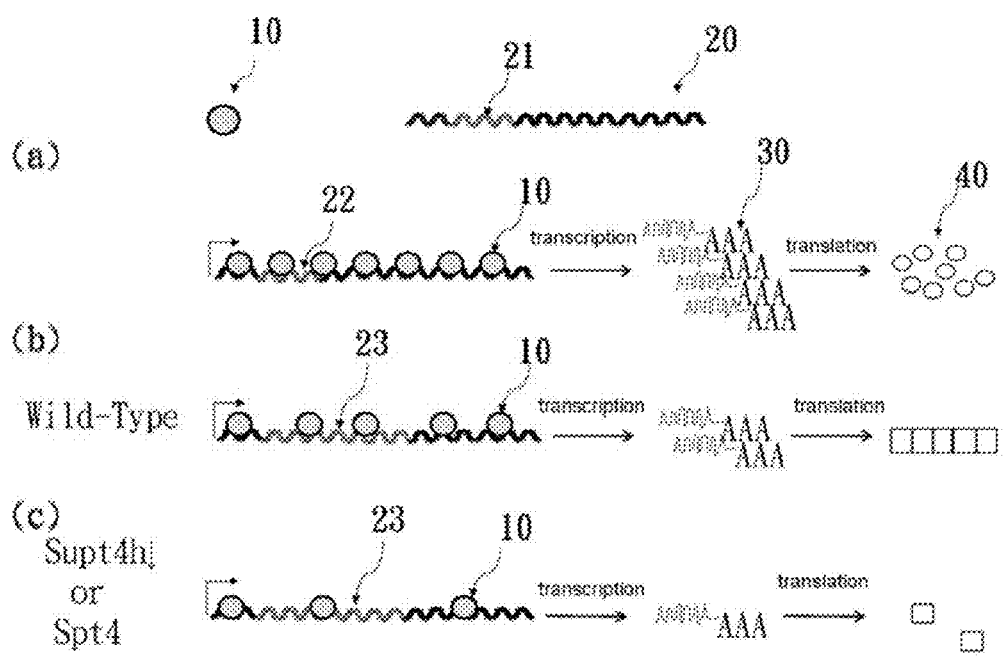
FIG. 1 illustrates the down-regulating effect that Spt4-/Supt4h-deficiency has on the expression of CAG-containing genes. (a) shows the gene transcription process starting with RNA Polymerase II (shown as speckle spheres) moving along a DNA template (shown as wavy lines) containing non-pathogenic number of CAG repeats (grey) to produce mRNA and then translated into protein products. (b) illustrates how proteins containing expanded number of glutamines can aggregate to form proteinacious deposits. (c) shows the attenuation effect of Supt4h- and Spt4-deficiency on the production of polyQ proteins when they are down-regulated.

The present invention will now be illustrated by specific exemplary embodiments and examples to facilitate a full understanding of the various ramifications. Although the present invention will be described in terms of specific exemplary embodiments and examples, it will be appreciated that the embodiments disclosed herein are for illustrative purposes only and various modifications and alterations might be made by those skilled in the art without departing from the spirit and scope of the invention as set forth in the appended claims.

Definitions

Throughout this disclosure, gene names are denoted with italicized capital letters, and the proteins associated with the genes are denoted in non-italicized letters with only the first letter capitalized. For example, for the SPT4 gene, the term "SPT4" denotes the gene and the term "Spt4" denotes the protein produced by the gene. The only exception is for the Huntingtin gene in which the gene name is denoted by "Htt" and the gene product (the protein huntingtin) is denoted by "Htt".

As used herein, the gene SPT4 refers to the gene that encodes the transcription elongation protein Spt4. The gene is characterized by (Malone et al., 1993), the entire content of which is incorporated herein by reference. The protein Spt4 is characterized by (Malone et al., 1993), the entire content of which is incorporated herein by reference.

As used herein, the gene SPT5 refers to the gene that encodes the transcription elongation protein Spt5. The gene is characterized by (Swanson et al., 1991), the entire content of which is incorporated herein by reference. The protein Spt5 is characterized by (Swanson et al., 1991), the entire content of which is incorporated herein by reference.

As used herein, the gene SUPT4H refers to the gene that encodes the mammalian transcription elongation factor Supt4h. The gene is characterized by (Hartzog et al., 1996; Chiang et al., 1996), the entire content of which is incorporated herein by reference. The protein Supt4h is characterized by (Hartzog et al., 1996; Chiang et al., 1996), the entire content of which is incorporated herein by reference.

As used herein, the gene SUPT5H refers to the gene that encodes the mammalian transcription elongation factor Supt5h. The gene is characterized by (Stachora et al., 1997; Chiang et al., 1998), the entire content of which is incorporated herein by reference. The protein Supt5h is characterized by (Stachora et al., 1997; Chiang et al., 1998), the entire content of which is incorporated herein by reference.

In the context of the present invention, the term "polyQ diseases" refer to the eight diseases listed in Table 1.

In the context of the present invention, the term "polyQ mutant protein" refers to proteins that have a polyQ tract longer than 36 glutamine residues.

In the context of the present invention, the term "expanded CAG repeats" refers to CAG repeat numbers greater than 36.

Methods for Suppressing the Expression of Genes Containing Expanded CAG Repeats

As explained above, the present invention provides a method for modulating the expression of a gene in a cell, wherein the gene contains expanded CAG repeats. Preferably, the number of CAG repeats is more than 36 copies. Genes that contain expanded CAG repeats are preferably selected from the group consisting of SCA1, SCA2, SCA3, SCA7, SCA17, DRPLA, AR, and Htt gene.

In some preferred embodiments, methods in accordance with this aspect of the present invention generally include the step of suppressing the expression of Spt4 in an yeast cell or Supt4h in a mammalian cell.

Means for suppressing the expression of the gene products are not particularly limited. They may be any commonly known gene silencing method in the art or other future developed gene suppression methods, so long as they are capable of suppressing the expression of the gene products (i.e. the Spt4 and Supt4h proteins). Exemplary gene silencing methods may include, but not limited to, gene knockdown, gene knock-out, or by use of a chemical reagent or a mixture thereof that is capable of suppressing the expression of the SPT4 or the SUPT4H gene.

In a preferred embodiment, the siRNA and gene knock-out are used to regulate the SUPT4H gene in a mammalian cell, and SPT4 gene in an yeast cell respectively. The RNA interference sequence used to effect gene knockdown is preferably a complementary gene sequence of SUPT4H, more preferably with a sequence homology of 80% or more.

Without being bound to any particular theory, it is believed that suppression of SPT4 and SUPT4H will diminish the cell's capability to generate gene transcripts with long CAG repeats, thereby attenuating the expression of proteins with expanded polyQ tracts.

FIG. 1 graphically illustrates the process by which Htt gene is transcribed and translated into Htt proteins.

Referring to FIG. 1(a), RNA polymerase II (grey spheres) 10 are shown moving along a DNA template with CAG repeats 21 (shown as a segment with slash) on a normal Htt gene 20. During transcription, the RNA polymerase II 10 becomes associated with a DNA template of the Htt gene 20 first, then moves along the template to generate mRNA of the gene that contains CAG repeats (that is, Htt gene mRNA) 30. The Htt protein 40 is subsequently generated by translating the Htt gene mRNA 30. In short, FIG. 1(a) shows what happens in the case of genes containing normal CAG repeats, or "short CAG repeats" 22.

FIG. 1(b) shows what happens in the case of mutated Htt gene 20 which contains expanded CAG repeats, or "long CAG repeats" 23. As mentioned above, when Htt proteins 40 are produced with a stretch of expanded polyQ repeats, it tends to aggregate and accumulate in organs or tissues, causing the HD phenotype.

In FIG. 1(c), the SUPT4H gene is down-regulated. As a result, polymerase II 10 becomes unable to associate persistently with the mutated Htt gene 20 during transcription elongation, which in turn leads to reduced production of the Htt proteins, thereby preventing or ameliorating the polyQ disease phenotype.

In addition to suppressing the expression of the transcription elongation factor genes SPT4 and SUPT4H, the same polyQ mutant protein attenuation effect can also be achieved by targeting directly at the Spt4 and Supt4h proteins or indirectly at their interaction partners. For example, Spt4 protein is known to associate with Spt5 protein to form a complex in yeast cells. Inventors have discovered that by disrupting the formation of the Spt4/Spt5 complex, expression of mutant polyQ proteins is also attenuated. Similarly, Supt4h and Supt5h also form a complex in mammalian cells (e.g. human cells). Therefore, inhibition of the two complexes is an alternative and practical way to suppress expression of CAG expanded genes and prevent polyQ aggregation in human or yeast cells.

Accordingly, in some preferred embodiments, methods in accordance with this aspect of the present invention generally include the step of disrupting the formation of a transcription elongation protein complex. Preferably, the transcription elongation protein complex is Spt4/Spt5 in yeast cells or Supt4h/Supt5h in mammalian cells.

Means for disrupting the formation of the protein complexes are not particularly limited. They can be achieved by any commonly known methods in the art, including, for example, by using a known or later developed inhibitor of Spt4 or Spt5 in the case of yeast cells, and Supt4h or Supt5h in the case of mammalian cells. Gene silencing methods such as siRNA, RNAi, or any other known gene-silencing methods in the art may also be advantageously used to suppress the expression of at least one factor in the corresponding complexes. For example, in the case of Spt4/Spt5, gene suppression of SPT4, SPT5, or both may be advantageously used to pre-empt the formation of the complex. Alternatively, mutant Spt4 or Spt5 may be introduced as disrupting agents to disrupt the formation of wild-type Spt4/Spt5 complex.

In other further embodiments, the gene suppression step may also be advantageously employed in conjunction with the protein complex disruption step. For example, in an exemplary embodiment, a method for modulating the expression of mutant polyQ proteins in a cell may include the step of suppressing the expression of the SPT4 gene for a yeast cell, or the SUPT4H gene for a mammalian cell; and the step of inhibiting the formation of Spt4/Spt5 complex in a yeast cell, or the Supt4h/Supt5h complex in a mammalian cell.

Methods for Treating polyQ Diseases

In yet another aspect, this invention also provides methods for treating a polyQ disease, wherein the polyQ disease is one selected from the group consisting of Spino-cerebellar ataxia type 1, 2, 3, 7, 17, dentatorubral-pallidoluysian atrophy, spinal and bulbar muscular atrophy, and Huntington's disease.

In some preferred embodiments, methods in accordance with this aspect of the present invention may include the general step of administering an effective amount of a gene silencing agent to suppress the expression of the SUPT4H gene, the SUPT5H gene, or both. The type of gene silencing agent is not particularly limited. Any gene silencing agent known in the art or future developed gene silencing agent may be used so long as the agent is capable of suppressing the expression of the SUPT4H or SUPT5H gene. Those skilled in the art will know that different gene silencing agent will require a suitably chosen route of administration. In an exemplary embodiment, the gene silencing agent is siRNA, RNAi, or D-RNAi.

In some other preferred embodiments, methods in accordance with this aspect of the present invention may include the general step of administering a pharmaceutical agent capable of disrupting the formation of the Supt4h/Supt5h complex. The pharmaceutical agent is also not particularly limited, so long as it is capable of disrupting the formation of the Supt4h/Supt5h complex in vivo. Suitable pharmaceutical agent may be a specific inhibitor of Supt4h or Supt5h. Exemplary pharmaceutical agent may include, but not limited to, small molecules, peptides, or antibodies. It may also be an engineered mutant of Supt4h or Supt5h.

Methods for Identifying Agents Useful as Lead Compounds

In still another aspect, this invention further provides a method for screening and identifying a lead compound for treating a polyQ disease. Methods in accordance with this aspect of the present invention generally include the step of testing a candidate compound's effectiveness at disrupting the formation of a protein complex, and identifying the compound as a lead compound If it is effective at a predetermined threshold amount.

The testing step may be performed with a protein-protein interaction assay for Spt4/Spt5 interaction or Supt4h/Supt5h interaction. Design of the protein-protein interaction assay is not particularly limited. For example, the protein-protein interaction resulting from the Spt4/Spt5 or Supt4h/Supt5h complex may be established, either in vitro or in vivo, using full-length or segment of these proteins. If the assay is an in vivo assay, it is preferably a yeast cell-based assay for Spt4/Spt5 interaction and a mammalian cell-based assay for Supt4h/Supt5h interaction.

The readout for the protein-protein interaction can be, for instance, a fluorescence signal, a FRET signal, or an enzymatic reaction.

Small molecules, peptides, or antibodies that interfere with this protein-protein interaction are selected as a candidate compound.

It is particularly noted that protein-protein based identification of lead compounds have been shown to be an effective general approach for lead compound identification. For example, it was known that MDM2 binds to and negatively regulates p53 for tumorigenesis. Nutlin-3, a small molecule showing effectiveness for cancer treatment, was identified by its capability to block the interaction between MDM2 and p53 protein (Vassilev et al., *Science*, 303:844-848, the entire content of which is incorporated herein by reference). This exemplary case, along with several other studies, provide support for the validity of protein-protein interaction based drug discovery methods as those disclosed herein.

In a preferred embodiment, the assay used is color colony assay previously developed by the inventors. Details of the assay is described in U.S. Pat. No. 7,375,190 B2, the entire content of which is incorporated herein by reference.

To further illustrate the present invention, the following specific examples are provided

EXAMPLES

Example 1

Mutant Htt mRNA Expression is Inhibited by Supt4h siRNA Knockdown

Murine striatal neural cell lines ST14A (rat), $Hdh^{Q7/Q7}$ (mouse), $Hdh^{Q111/Q111}$ (mouse), and $Hdh^{Q7/Q111}$ (mouse) were cultured in Dulbecco's modified Eagle's medium (SH30022, HyClone) supplemented with 10% fetal bovine serum (FBS) at 33° C. with 5% $CO_2$. ST14A was transfected with pTet-Off plasmid (BD Biosciences) to establish the stable cell line ST14Atet, which expressed pTRE2-7Q-eGFP or pTRE2-81Q-eGFP in the absence of tetracycline. DNA and siRNA transfections were carried out using LipofectAMINE 2000 (Invitrogen). 100 nM of Supt4h siRNA (DHARMACON, ON-TARGET plus SMART pool, L-048866-01 that include 5' -CUAUAGACCAGUUC-GAAUA-3' (SEQ ID 1), 5'-UCAAAUAC-CAAUAAAGCGA-3'(SEQ ID 2), 5'-GGGAGUGU-CUGGGCGGAUU-3' (SEQ ID 3), 5' -CCCAAGGAAU CGUGCGGGA-3' (SEQ ID 4)) and (DHARMACON, J-086342-10, 5'-UGGCCUACAAAUCGAGAGAUU-3' (SEQ ID 5)) were used to inhibit expression of Supt4h in mice and rat cells, respectively. Transfection of an equivalent amount of annealed double-stranded oligonucleotides (5'-UUCUCCGAACGUGUCACGUTT-3' (SEQ ID 6) and 5'-ACGUGACACGUUCGGAGAATT-3' (SEQ ID 7)) that do not target any gene served as a control.

Figure 2A:
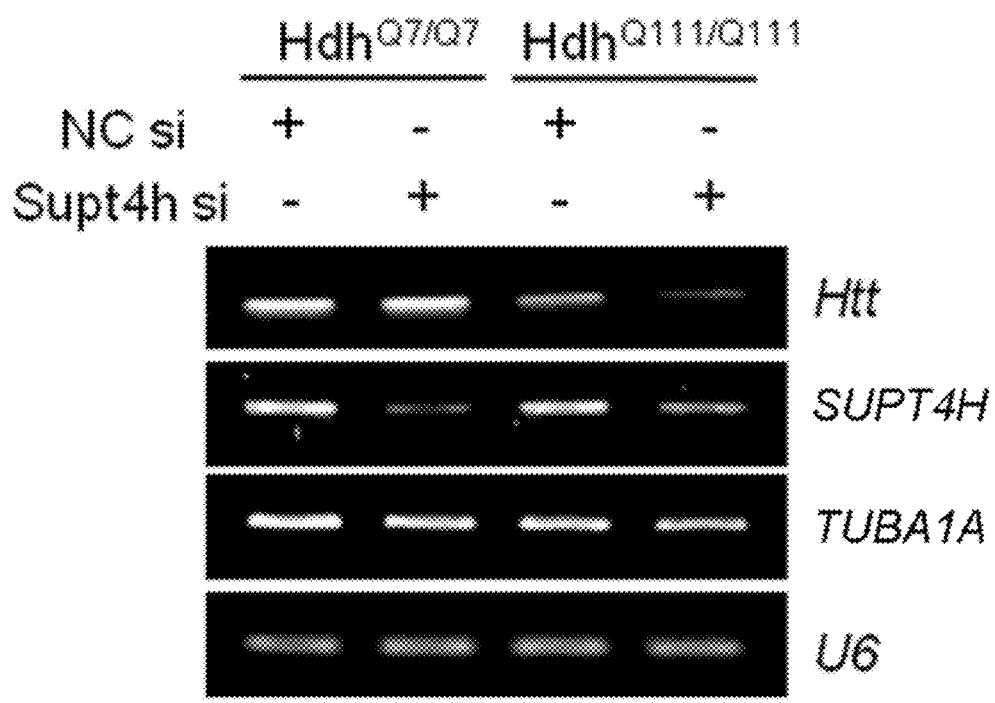
FIG. 2A shows the level of Htt mRNA expression following Supt4h siRNA knockdown in striatal cells as determined by RT-PCR.

In FIG. 2A, Htt mRNA levels were examined by RT-PCR following Supt4h siRNA knockdown in striatal cells possessing homozygous wild-type ($Hdh^{Q7/Q7}$) or mutant huntingtin alleles ($Hdh^{Q111/Q111}$). U6, which is transcribed by RNA polymerase III, served as loading control. TUBA1A was included to examine the effect of Supt4h on pol II-dependent transcription of housekeeping genes. It shows that the mutant Htt mRNA level is decreased in response to SUPT4H gene knockdown in $Hdh^{Q111/Q111}$ cells. However, with similar extent of SUPT4H down-regulation, there is no detectable change in the expression of normal Htt mRNA in $Hdh^{Q7/Q7}$.

Figure 2B:
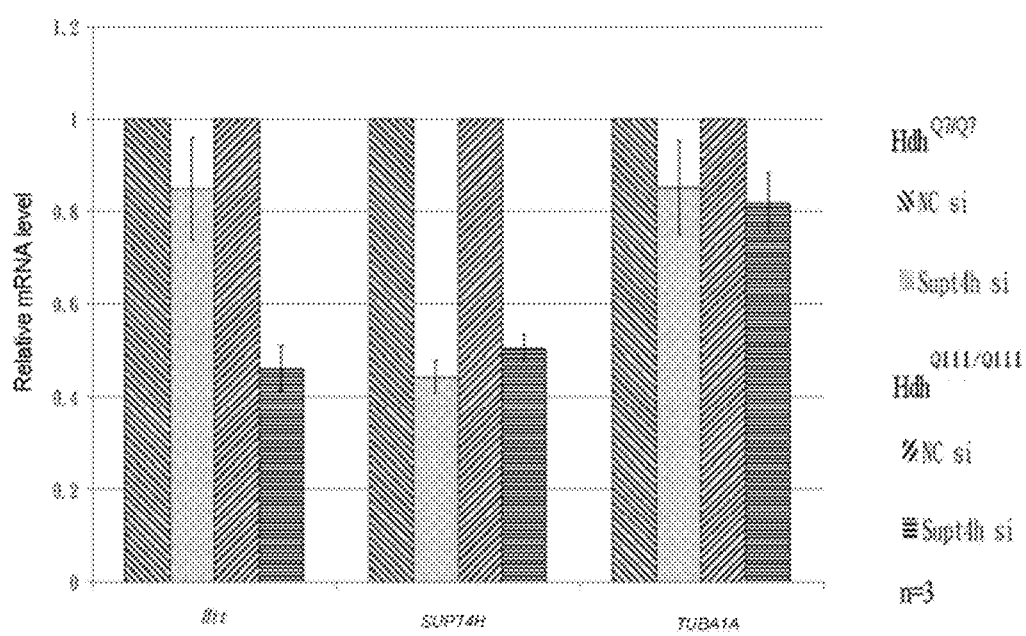
FIG. 2B shows the changes in the level of Htt mRNA expression following Supt4h siRNA knockdown as assessed by real-time qRT-PCR.

In FIG. 2B, changes in the level of mRNA expression following Supt4h siRNA knockdown were assessed by real-time qRT-PCR. Each mRNA was normalized with U6 and transcript levels in cells transfected with control siRNA (NC siRNA) were set as 1. In this figure, the horizontal axis represent the Htt gene, SUPT4H gene, TUBA1A gene, and the longitudinal axis represent the relative mRNA level. It shows that the level of mutant Htt mRNA in $Hdh^{Q111/Q111}$ is substantially reduced, while there is only slight decrease of normal Htt mRNA in $Hdh^{Q7/Q7}$ by SUPT4H gene knockdown.

Both FIGS. 2A and 2B show that expression of the mutant Htt gene is regulated by Supt4h.

Example 2

Figure 3:
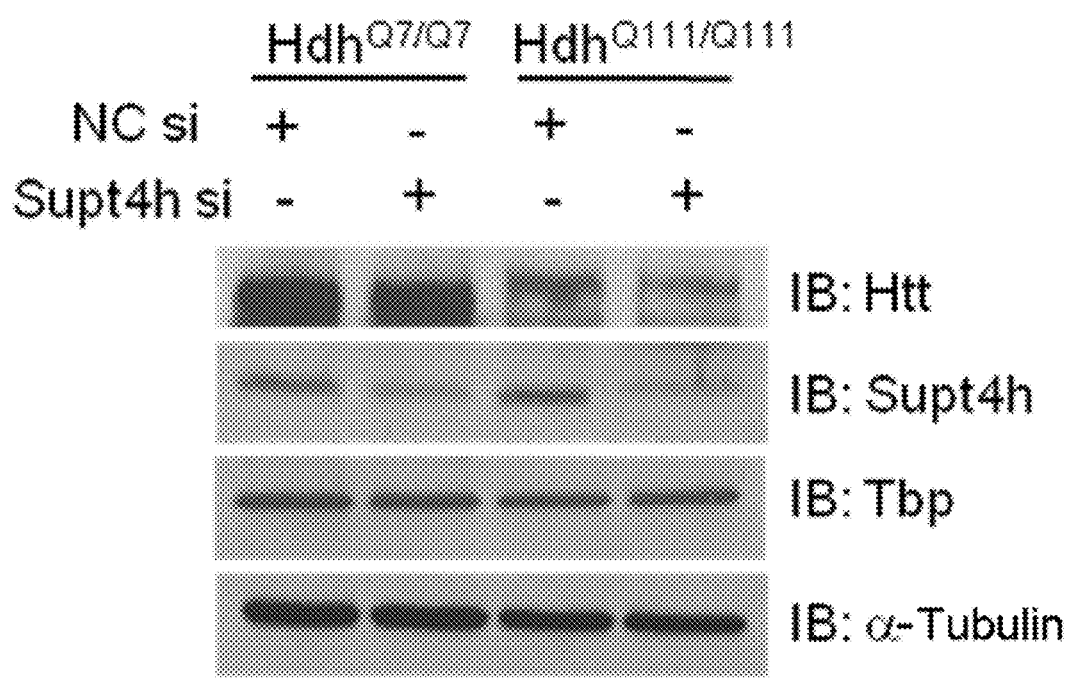
FIG. 3 shows the level of protein expression in cells with and without Supt4h siRNA transfection.

Analysis of Htt Protein Expression in Cells with and without Supt4h siRNA Knockdown In FIG. 3, cell lysates collected from Example 1 were analyzed by immunoblot to determine the change of proteins expression in response to Supt4h siRNA knockdown. Equal amounts of total protein extracts were immunoblotted for Htt, Supt4h, Tbp, and α-Tubulin. Tbp, the TATA-box binding protein, was included as a representative of protein coding genes with a short stretch of CAG repeats.

It shows that the level of mutant Htt protein is lower in $Hdh^{Q111/Q111}$ cells treated with Supt4h siRNA, compared to the one treated with NC siRNA. The decrease in mutant Htt protein is consistent with the change of corresponding mRNA in $Hdh^{Q111/Q111}$ cells as observed in Example 1. In addition, the protein level of encoding genes with normal CAG repeats (the CAG trinucleotide repeat number is less than 36), such as $Htt^{Q7}$ and Tpb protein, is not affected by Supt4h siRNA knockdown.

Example 3

SUPT4H Gene Down-Regulation Inhibits Mutant but not Normal Htt Expression

Figure 4:
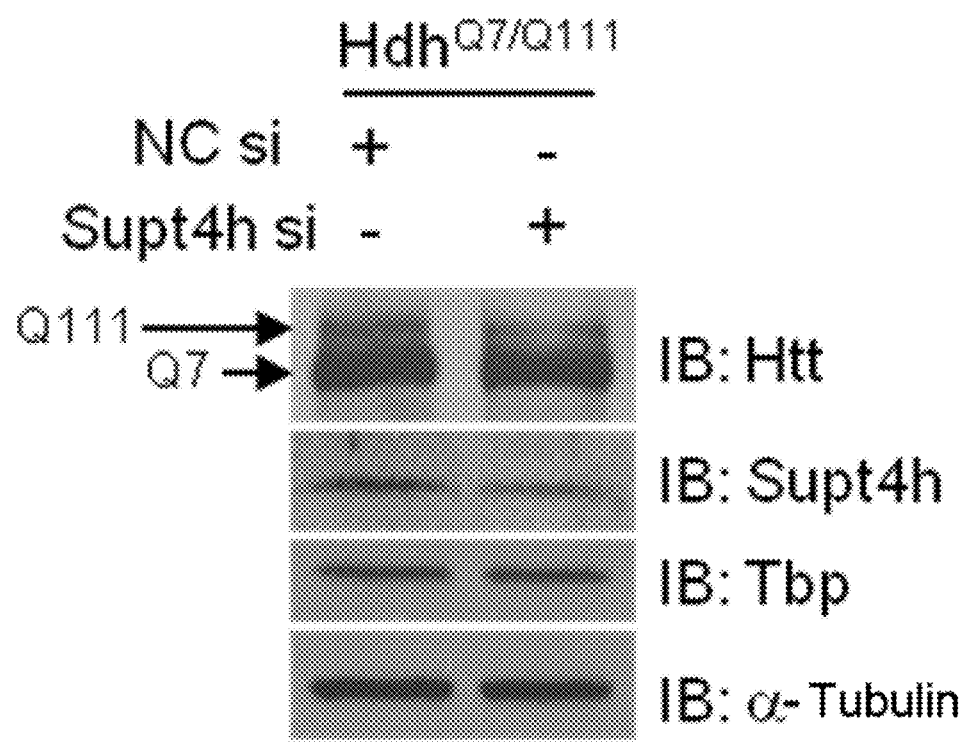
FIG. 4 shows the effects of Supt4h down-regulation on the expressions of normal and mutant Htt, respectively.

In FIG. 4, striatal cells with heterozygous Htt alleles ($Hdh^{Q7/Q111}$) were transfected with Supt4h siRNA and protein expression was analyzed as described in Example 2. The positions of $Htt^{Q7}$ and $Htt^{Q111}$ are indicated by arrows. In response to SUPT4H knockdown, the protein level of $Htt^{Q111}$ is decreased but the protein level of $Htt^{Q7}$ remains unchanged. It further confirms that only genes containing expanded CAG repeats are affected by Supt4h.

Example 4

Figure 5:
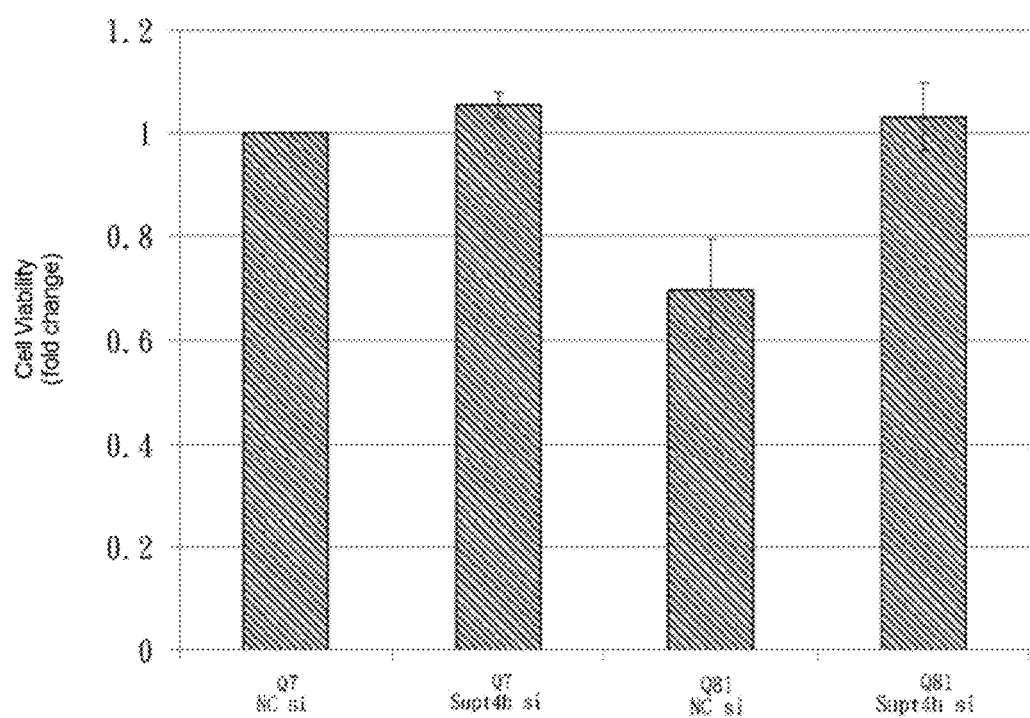
FIG. 5 shows the viability of ST14A striatal cells expressing 7Q-eGFP or 81Q-eGFP with or without Supt4h siRNA knockdown.

Viability of ST14a Cells Expressing 81Q-eGFP is Improved by Supt4h siRNA Knockdown Viability of ST14A cells expressing 7Q-eGFP or 81Q-eGFP was measured with and without Supt4h siRNA knockdown. After transfection with indicated polyQ-eGFP and siRNA, cells were cultured in growth media containing a minimal amount (0.5%) of serum and maintained at 39° C. to induce neuronal cell differentiation. The number of viable cells expressing 7Q-eGFP in the presence of control siRNA was set as 1, and the relative cell viability of other samples is illustrated in FIG. 5. Compared to cells transfected with 7Q-eGFP, ST14A transfected with 81Q-eGFP showed a reduction in cell viability that was reversed by siRNA-mediated SUPT4H knockdown. By contrast we observed no effect of Supt4h siRNA on survival of cells expressing 7Q-eGFP. It demonstrates the reduction of cell viability caused by expression of aggregation-prone proteins that contain expanded polyQ repeats can be ameliorated by SUPT4H gene down-regulation.

Example 5

Figure 6:
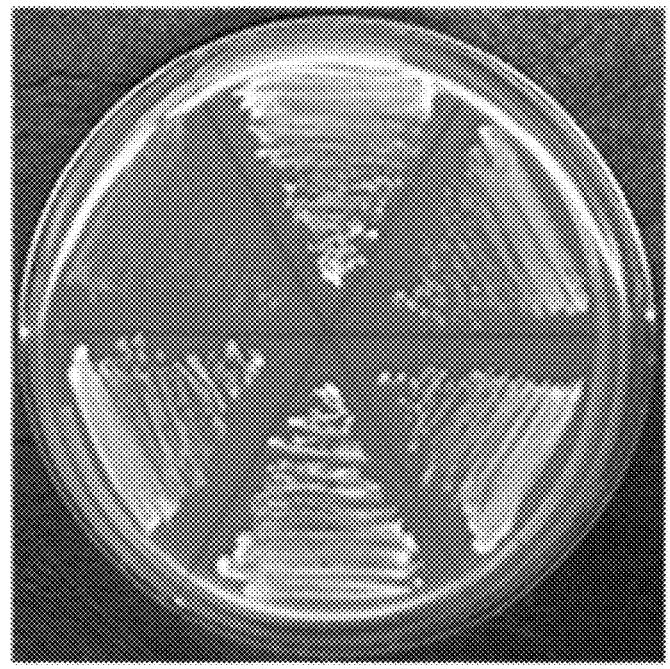
FIGS. 6(a) and 6(b) illustrate that SPT4 deletion or SPT5 mutant which inhibits Spt4/Spt5 complex formation can suppress the expression of genes containing expanded CAG repeats, leading to reduced polyQ aggregation as revealed by colony color assay.
Figure 6:
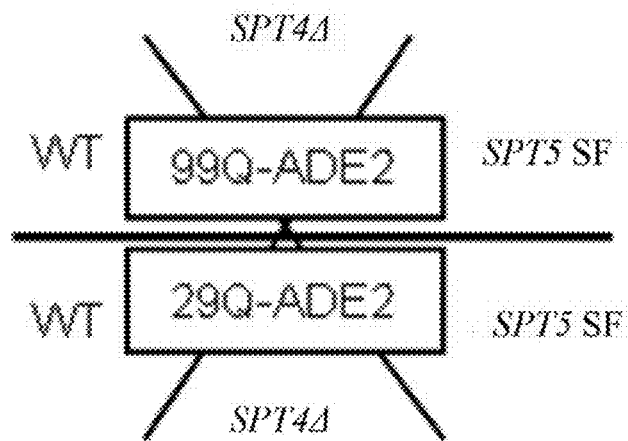

Inhibition of polyQ Aggregation by Preventing the Formation of Spt4/Spt5 Complex in Yeast Cells To this end, we used colony color assay that is developed by our laboratory (U.S. Pat. No. 7,375,190 B2) to determine the aggregation of polyQ-containing proteins. In this assay system, the reporter protein Ade2 is fused with either a stretch of 29Q or 99Q. When the fusion protein is soluble, it is functional and the Ade2 enzymatic activity makes cell color white. In contrast, if the protein is aggregated, Ade2 becomes defective and cell color turns red. 29Q-Ade2 can not aggregate due to its short polyQ repeats (less than 36Q) and is included as a representative of genes with short CAG trinucleotide repeats such as normal Htt gene. In FIG. 6, it is evident that wild-type (WT) cells expressing 29Q-ADE2 and 99Q-ADE2 show white and red color respectively. However, the red cell color is changed to white in 99Q-ADE2 expression cells when SPT4 gene deletion (SPT4Δ) or SPT5 SF mutant is introduced in these cells. SPT5 SF cells carry a specific SPT5 S324F point mutation that inhibits formation of a Spt4/Spt5 complex. These results indicate polyQ aggregation is affected by interfering the formation of Spt4/Spt5 complex.

Example 6

Figure 7:
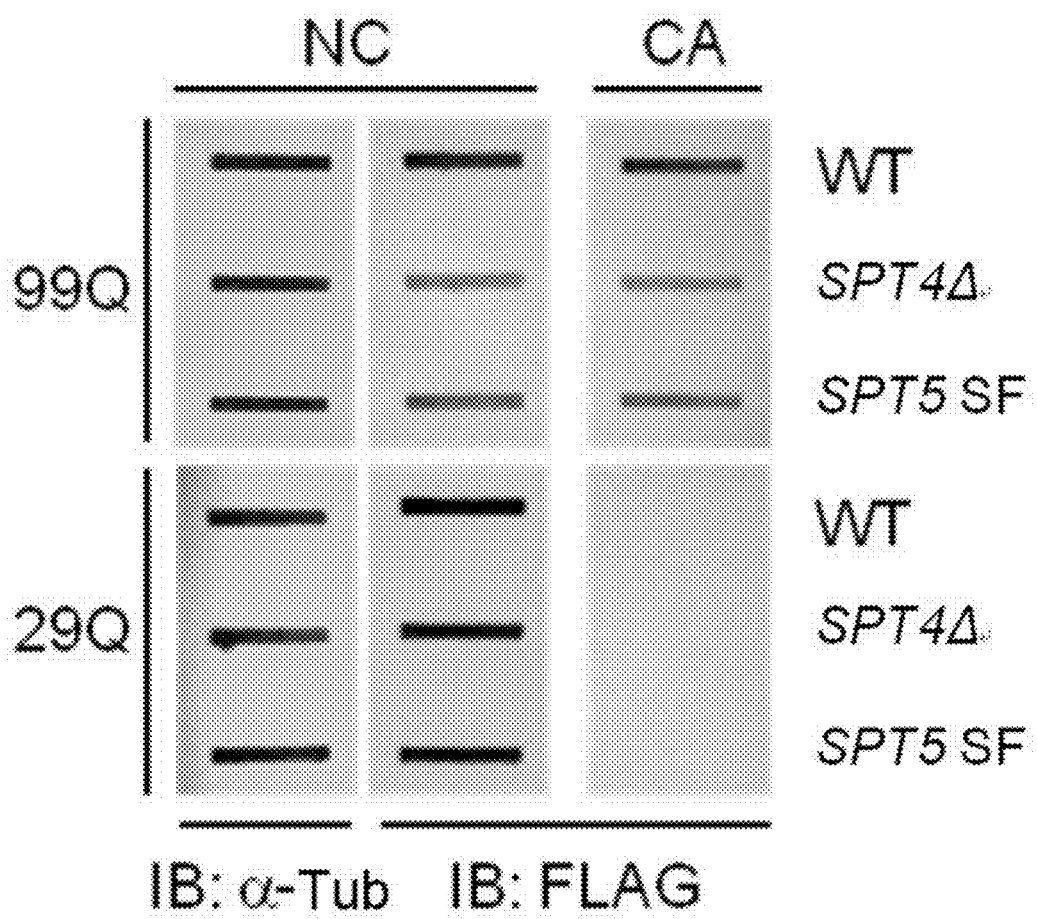
FIG. 7 illustrates the changes in the expression and aggregation patterns of polyQ mutant proteins resulting from inhibiting the formation of Spt4/Spt5 complex.

Analysis of polyQ-Ade2 Protein Expression and Aggregation in Cells with SPT4 Gene Deletion or SPT5 SF Mutation PolyQ-Ade2 protein expression and aggregation were examined by slot blot and filter-trap assays, respectively. Filter-trap assay used a cellulose acetate (CA) membrane to trap only aggregated protein, while slot blot assay used a nitrocellulose (NC) membrane that retains all loading proteins. Retention of polyQ-Ade2 on the membranes was detected by immunoblot using anti-FLAG antibody. α-Tubulin (α-Tub) was included to ensure equivalent protein loading in each sample. In FIG. 7, it shows 99Q-Ade2 protein aggregation (CA, top panel) is greatly reduced in SPT4d and SPT5 SF mutant cells compared to WT cells. This finding is consistent with the notion that these mutant cells have less polyQ aggregation as observed in Example 5. Beside reduced aggregation, we also found the 99Q-Ade2 protein expression (NC, top panel) is decreased in SPT4Δ and SPT5 SF cells. However, these mutant cells did not affect the expression of 29Q-Ade2 (NC, bottom panel). These results confirm that it is practical to inhibit polyQ aggregation by interfering the formation of Spt4/Spt5 complex. In addition, expression of proteins with a long stretch of polyQ (>36Q) but not the short one is susceptible to mutations that prevent the formation of Spt4/Spt5 complex.

Example 7

Figure 8:
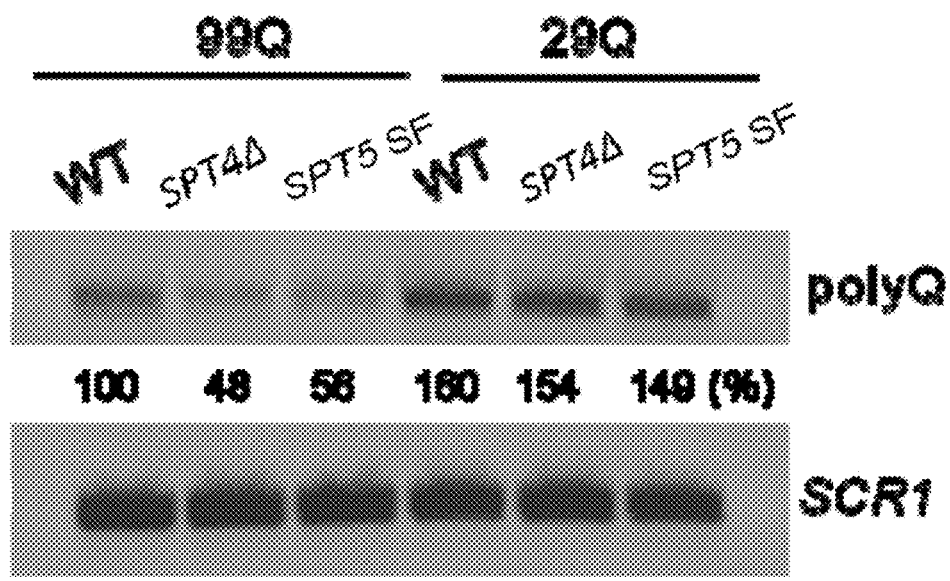
FIG. 8 shows the reduced expression of transcripts containing expanded CAG repeats resulting from inhibiting the formation of Spt4/Spt5 complex.

Analysis of polyQ-ADE 2 mRNA Levels by Northern Blot in Cells with SPT4 Gene Deletion or SPT5 SF Mutation Expression of transcripts encoding 99Q-Ade2 and 29Q-Ade2 was analyzed by Northern blot in cells as described in Example 5. polyQ-ADE2 mRNAs were detected by polyQ probe and SCR1 was included as a loading control. After normalization, the mRNA level in WT cells expressing 99Q-ADE2 was set at 100%. Relative 99Q-ADE2 and 29Q-ADE2 mRNA levels in indicated cells are illustrated in FIG. 8. Compared to WT, both SPT4Δ and SPT5 SF cells show decreased 99Q-ADE2 but not 29Q-ADE2 mRNA expression. This observation is in agree with the change of 99Q-Ade2 protein expression in SPT4Δ and SPT5 SF mutant cells in Example 6.

This finding also validates that it is practical to inhibit the expression of genes with expanded CAG repeats without affecting the one encoding short polyQ repeats by interfering the formation of Spt4/Spt5 complex.

What is claimed is:

1. A method of modulating the expression of a first gene in a cell, comprising:
administering an inhibitor that specifically targets Spt4/Spt5 or Supt4h/Supt5h, thereby inhibiting formation of a Spt4/Spt5 or Supt4h/Supt5h complex in the cell, wherein said first gene is one containing expanded CAG repeats with more than 36 repeats and said inhibitor is selected from the group consisting of an antibody, a small reagent, or a peptide.

2. The method of claim 1, wherein said first gene encodes a protein containing a polyglutamine stretch with more than 36 glutamine residues and form aggregates in the cell.

3. The method of claim 1, wherein the first gene is selected from the group consisting of SCA1, SCA2, SCA3, SCA7, SCA17, DRPLA, AR, and Htt gene.

4. The method of claim 1, wherein said cell is an animal cell or an yeast cell.

5. The method of claim 4, wherein said cell is a mammalian cell.

6. A method of treating a polyglutamine disease, comprising:
applying the method of claim 1 to a subject suffering from said polyglutamine disease.

7. The method of claim 6, wherein said polyglutamine disease is selected from the group consisting of Spino-cerebellar ataxia type 1, 2, 3, 7, 17, dentatorubral-pallidoluysian atrophy, spinal and bulbar muscular atrophy, and Huntington's disease.

* * * * *